US011490783B2

(12) United States Patent
Masuno et al.

(10) Patent No.: US 11,490,783 B2
(45) Date of Patent: Nov. 8, 2022

(54) ENDOSCOPE SYSTEM AND METHOD OF OPERATING SAME

(71) Applicant: FUJIFILM Corporation, Tokyo (JP)

(72) Inventors: Shingo Masuno, Kanagawa (JP); Yusuke Kurioka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

(21) Appl. No.: 16/526,984

(22) Filed: Jul. 30, 2019

(65) Prior Publication Data

US 2019/0350438 A1 Nov. 21, 2019

Related U.S. Application Data

(63) Continuation of application No. PCT/JP2018/001321, filed on Jan. 18, 2018.

(30) Foreign Application Priority Data

Feb. 1, 2017 (JP) .............................. JP2017-016436

(51) Int. Cl.
*A61B 1/00* (2006.01)
*A61B 1/06* (2006.01)
(Continued)

(52) U.S. Cl.
CPC ...... *A61B 1/00009* (2013.01); *A61B 1/00165* (2013.01); *A61B 1/053* (2013.01);
(Continued)

(58) Field of Classification Search
CPC . A61B 1/00009; A61B 1/00165; A61B 1/053; A61B 1/0638; A61B 1/0684;
(Continued)

(56) References Cited

U.S. PATENT DOCUMENTS 4,171,513 A * 10/1979 Otey ......................... H04K 1/02
375/354
10,441,133 B2 * 10/2019 Kasumi ............... A61B 1/00036
(Continued)

FOREIGN PATENT DOCUMENTS

| CN | 101313838 | 12/2008 |
| CN | 103339924 | 10/2013 |

(Continued)

OTHER PUBLICATIONS

"Office Action of China Counterpart Application", dated Apr. 29, 2021, with English translation thereof, pp. 1-17.
(Continued)

*Primary Examiner* — Anh Tuan T Nguyen
*Assistant Examiner* — Shankar Raj Ghimire
(74) *Attorney, Agent, or Firm* — JCIPRNET (57) ABSTRACT

An endoscope system includes at least any one of a processor device that is attachable to and detachable from an endoscope or a light source device that is attachable to and detachable from the endoscope. In a case where the endoscope is mounted on the processor device or the light source device, the processor device or the light source device performs a request sequence in which a request signal, for requesting a start of execution of encoding processing with respect to digital image signals, is transmitted to the endoscope.

11 Claims, 9 Drawing Sheets

(51) Int. Cl.
*A61B 1/05* (2006.01)
*A61B 90/00* (2016.01)
*A61B 17/00* (2006.01)

(52) U.S. Cl.
CPC .......... *A61B 1/0638* (2013.01); *A61B 1/0684* (2013.01); *A61B 1/00006* (2013.01); *A61B 1/00027* (2013.01); *A61B 17/00234* (2013.01); *A61B 90/361* (2016.02)

(58) Field of Classification Search
CPC .............. A61B 90/361; A61B 1/00006; A61B 1/00027; A61B 17/00234; H04N 2005/2255
See application file for complete search history.

(56) References Cited

U.S. PATENT DOCUMENTS

| | | | | |
|---|---|---|---|---|
| 2002/0177751 | A1* | 11/2002 | Ueno | A61B 1/045 600/160 |
| 2003/0202090 | A1* | 10/2003 | Ota | A61B 1/045 348/69 |
| 2007/0070194 | A1* | 3/2007 | Abe | A61B 1/00016 348/72 |
| 2007/0299301 | A1 | 12/2007 | Uchiyama et al. | |
| 2008/0139881 | A1* | 6/2008 | Cover | A61B 1/04 600/103 |
| 2009/0062612 | A1 | 3/2009 | Suda | |
| 2009/0073260 | A1* | 3/2009 | Nagase | A61B 1/00016 348/68 |
| 2009/0213212 | A1* | 8/2009 | Nakamura | A61B 1/00006 348/65 |
| 2012/0075449 | A1* | 3/2012 | Yasuda | A61B 1/0638 348/68 |
| 2013/0096376 | A1* | 4/2013 | Takei | A61B 1/063 600/103 |
| 2013/0096380 | A1* | 4/2013 | Matsuzawa | G02B 23/2484 600/109 |
| 2013/0123578 | A1* | 5/2013 | Gocho | A61B 1/00059 600/109 |
| 2013/0176409 | A1* | 7/2013 | Kotani | A61B 1/00009 348/65 |
| 2013/0235173 | A1* | 9/2013 | Segawa | A61B 1/00018 348/65 |
| 2014/0160259 | A1* | 6/2014 | Blanquart | A61B 1/317 348/65 |
| 2014/0171737 | A1* | 6/2014 | Kagaya | H04N 5/2327 600/109 |
| 2015/0216398 | A1* | 8/2015 | Yang | G01J 3/0208 600/109 |
| 2017/0084031 | A1* | 3/2017 | Iwasaki | A61B 6/469 |
| 2017/0290496 | A1* | 10/2017 | Fukuda | A61B 1/0638 |
| 2019/0069760 | A1* | 3/2019 | Hygelund | A61B 1/00105 |
| 2019/0110676 | A1* | 4/2019 | Urakawa | G02B 23/26 |
| 2019/0350438 | A1* | 11/2019 | Masuno | G02B 23/24 |

FOREIGN PATENT DOCUMENTS

| | | | | |
|---|---|---|---|---|
| EP | 2096865 | | 9/2009 | |
| EP | 3195791 | | 7/2017 | |
| FR | 3011996 | A1 * | 4/2015 | ............ H04L 25/03 |
| JP | 2003189300 | | 7/2003 | |
| JP | 2006149668 | | 6/2006 | |
| JP | 2009201540 | | 9/2009 | |
| JP | 2013150666 | | 8/2013 | |
| JP | 2015047459 | | 3/2015 | |
| WO | 2013031514 | | 3/2013 | |

OTHER PUBLICATIONS

"Search Report of Europe Counterpart Application", dated Jan. 17, 2020, p. 1-p. 7.

Office Action of Japan Counterpart Application, with English translation thereof, dated Mar. 31, 2020, pp. 1-8.

"International Search Report (Form PCT/ISA/210) of PCT/JP2018/001321," dated Feb. 13, 2018, with English translation thereof, pp. 1-5.

"Written Opinion of the International Searching Authority (Form PCT/ISA/237) of PCT/JP2018/001321," dated Feb. 13, 2018, with English translation thereof, pp. 1-10.

* cited by examiner

|  |  | ENDOSCOPE | |
|---|---|---|---|
|  |  | SCRAMBLE PROCESSING "WITHOUT" | DESCRAMBLE PROCESSING "WITH" |
| PROCESSOR DEVICE | DESCRAMBLE PROCESSING "WITH" | DESCRAMBLE PROCESSING "STOP" | SCRAMBLE PROCESSING DESCRAMBLE PROCESSING "EXECUTE" |
| | DESCRAMBLE PROCESSING "WITHOUT" | | SCRAMBLE PROCESSING "STOP" |

ENDOSCOPE SYSTEM AND METHOD OF OPERATING SAME

CROSS-REFERENCE TO RELATED APPLICATIONS

This application is a Continuation of PCT International Application No. PCT/JP2018/001321 filed on 18 Jan. 2018, which claims priority under 35 U.S.C § 119(a) to Japanese Patent Application No. 2017-016436 filed on 1 Feb. 2017. The above application is hereby expressly incorporated by reference, in its entirety, into the present application.

BACKGROUND OF THE INVENTION

1. Field of the Invention

The present invention relates to an endoscope system that transmits digital image signals in a serial manner, and a method of operating the same.

2. Description of the Related Art

In the medical field, diagnosis using an endoscope system comprising an endoscope, a light source device, and a processor device is general. The endoscope has an insertion part to be inserted into a subject, and images an observation target (mucous membrane or the like within the subject) irradiated with illumination light generated from the light source device. The processor device creates an image of the observation target by using digital image signals obtained by imaging the observation target, and displays the created image on a monitor.

The digital image signals obtained by the endoscope are transmitted to the processor device via a signal cable or the like. Transmission methods of the digital image signals mainly include a parallel method of transmitting the signals in a bit group in which a plurality of bits are combined, and a serial method of transmitting the signals bit by bit. In a case where priority is given to transmitting the digital image signals at a high speed, many serial methods are adopted (for example, WO2013/031514A (corresponding to US2013/0235173A1)).

SUMMARY OF THE INVENTION

By adopting a serial method as a communication method for the digital image signals, communication can be made at a high speed. However, in a case where fixed values are consecutively transmitted, electro-magnetic interference (electromagnetic radiation interference, so-called, electro-magnetic interference (EMI) to be emitted to the outside of a device by an apparatus) may be generated. In a case where there is regularity that fixed values are consecutive as a data transmission aspect, energy concentrates on a multiplied frequency of a serial communication clock, and the energy beyond the standard is electromagnetically discharged.

As described above, as a cause of consecutive fixed values during serial communication, it is conceivable that halation occurs in the observation target, and pixels in a region where the halation has occurred are saturated, and thereby, the highest pixel values are consecutively generated. Additionally, even among the digital image signals, fixed values, such as "0", are consecutive in a line blank region and a frame blank region that do not have image information on the observation target. Therefore, this also becomes a cause that the electro-magnetic interference is emitted.

Thus, it is conceivable to perform scramble processing by random number processing or the like so that the fixed values are not consecutive in the digital image signals. By transmitting the scramble-processed digital image signals, it is possible to avoid generation of electro-magnetic interference. The scrambled digital image signals are subjected to descramble processing and restored in order to perform imaging of the observation target.

In actual medical spots where endoscopes are used, various types of new and old endoscopes are used. For example, a situation in which an endoscope having a function of the scramble processing and an endoscope having no function of the scramble processing are used in a mixed manner is also considered. In a case where the endoscope having no function of the scramble processing is mounted on the processor device having the function of the descramble processing and is used, the descramble processing is performed even though the scramble processing is not performed on the digital image signals. In this case, an image of the observation target is influenced by performing unnecessary descramble processing. Thus, avoiding the generation of the electro-magnetic interference without influencing the image of the observation target is required.

An object of the invention is to provide an endoscope system and a method of operating the same that can avoid occurrence of electro-magnetic interference without influencing an image of an observation target.

An endoscope system of the invention comprises at least any one of a processor device that is attachable to and detachable from an endoscope or a light source device that is attachable to and detachable from the endoscope. In a case where the endoscope is mounted on the processor device or the light source device, a request sequence is performed in which a request signal, for requesting a start of execution of encoding processing with respect to digital image signals, is transmitted from the processor device or the light source device to the endoscope.

It is preferable that, in a case where the endoscope comprises an encoding processing unit that performs the encoding processing, the encoding processing unit starts execution of the encoding processing with reception of the request signal as a trigger, and performs an initial transmission sequence in which digital image signals are transmitted to the processor device or the light source device. It is preferable that that the initial transmission sequence includes a first transmission sequence in which specific signal processing is performed on a specific region other than an image data region having image information on an observation target in the digital image signals, and the digital image signals subjected to the specific signal processing are transmitted to the processor device or the light source device, and a second transmission sequence in which the encoding processing is performed on the digital image signals after the first transmission sequence, and the digital image signals subjected to the encoding processing are transmitted to the processor device or the light source device. It is preferable that the specific signal processing is incremental processing. It is preferable that the specific region is a line blank region or a frame blank region.

It is preferable that the endoscope system further comprises a light quantity calculation unit that calculates the quantity of light in an observation target on the basis of the digital image signals, and the encoding processing unit switches between execution and stop of the encoding processing depending on the quantity of light. It is preferable that the encoding processing unit stops the encoding processing in a case where the quantity of light is less than a fixed value, and executes the encoding processing in a case where the quantity of light is equal to or more than the fixed value. It is preferable that the endoscope system further comprises a delimiting signaling processing unit that performs delimiting signaling processing in which delimiter signals are applied to the digital image signals subjected to the encoding processing at regular intervals.

It is preferable that, in a case where the processor device or the light source device comprises a decoding processing unit that performs decoding processing on the digital image signals subjected to the encoding processing, the decoding processing unit starts execution of the decoding processing with reception of the digital image signals subjected to the encoding processing as a trigger. It is preferable that in a case where the endoscope does not comprise an encoding processing unit that performs the encoding processing, and the processor device or the light source device comprises a decoding processing unit that performs decoding processing on the digital image signals subjected to the encoding processing, the decoding processing unit stops execution of the decoding processing with reception of the digital image signals as a trigger. It is preferable that the encoding processing is scramble processing including pseudo-random number subtraction processing in which a pseudo-random number is subtracted from the digital image signals.

In a method of operating an endoscope system including at least any one of a processor device that is attachable to and detachable from an endoscope or a light source device that is attachable to and detachable from the endoscope, the method comprises a step of performing, by the processor device or the light source device, a request sequence in which a request signal for requesting a start of execution of encoding processing with respect to digital image signals is transmitted to the endoscope in a case where the endoscope is mounted on the processor device or the light source device.

According to the invention, generation of electro-magnetic interference can be avoided without influencing the image of the observation target.

DESCRIPTION OF THE PREFERRED EMBODIMENTS

Figure 1:
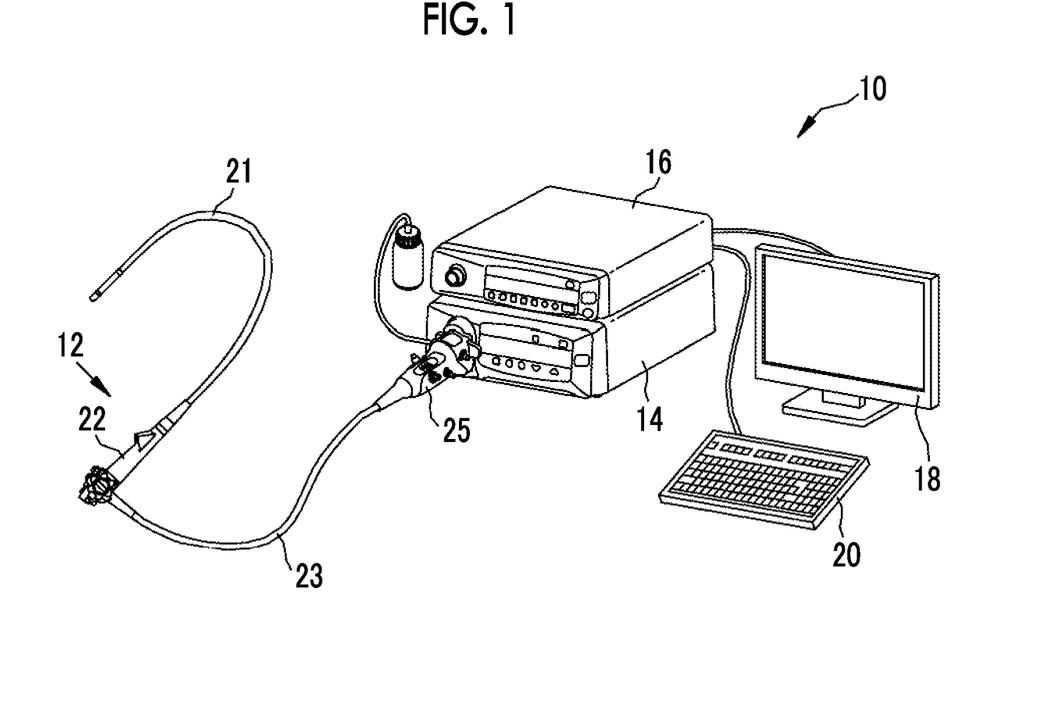
FIG. 1 is an external view of an endoscope system.

As illustrated in FIG. 1, the endoscope system 10 has an endoscope 12, a light source device 14, a processor device 16, a monitor 18, and a console 20. The endoscope 12 has an insertion part 21 to be inserted into a subject, an operating part 22 provided at a proximal end portion of the insertion part 21, and a universal cable 23. The universal cable 23 is a cable in which a light guide part 31 (refer to FIG. 2) for guiding illumination light emitted by the light source device 14, a control line for transmitting control signals used for control of the endoscope 12, a signal line for transmitting image signals obtained by imaging an observation target, a power line for supplying electrical power to the respective units of the endoscope 12, and the like are integrated with each other. A distal end of the universal cable 23 is provided with a connector 25 connected to the light source device 14. Additionally, the light guide part 31 of the endoscope 12 is a light guide in which optical fibers are bundled.

The light source device 14 generates the illumination light by, for example, a semiconductor light source, such as a light emitting diode (LED) or a laser diode (LD), a xenon lamp, or a halogen lamp. In a case where the connector 25 is connected to the light source device 14, the illumination light enters the light guide part 31 of the connector 25, and is applied from a distal end of the insertion part 21 to the observation target.

Additionally, the light source device 14 is electrically connected to the processor device 16, and the connector 25 of the endoscope 12 is connected to the processor device 16 via the light source device 14. Transmission and reception of the control signals, the image signals, or the like between of the light source device 14 and the connector 25 are wireless communication. For this reason, the light source device 14 wirelessly transmits the control signals, which are transmitted to and received from the connector 25, to the processor device 16. Moreover, although the light source device 14 supplies the electrical power for driving the endoscope 12 to the connector 25, the supply of the electrical power is also wirelessly performed.

The processor device 16 controls the quantity and emission timing of the illumination light emitted by the light source device 14 and the respective units of the endoscope 12, and creates an endoscopic image using the image signals obtained by imaging the observation target irradiated with the illumination light. Additionally, the processor device 16 is electrically connected to the monitor 18 and the console 20. The monitor 18 displays the endoscopic image generated by the processor device 16, information on the endoscopic image, and the like. The console 20 is a user interface that receives input operations, such as function settings.

Figure 2:
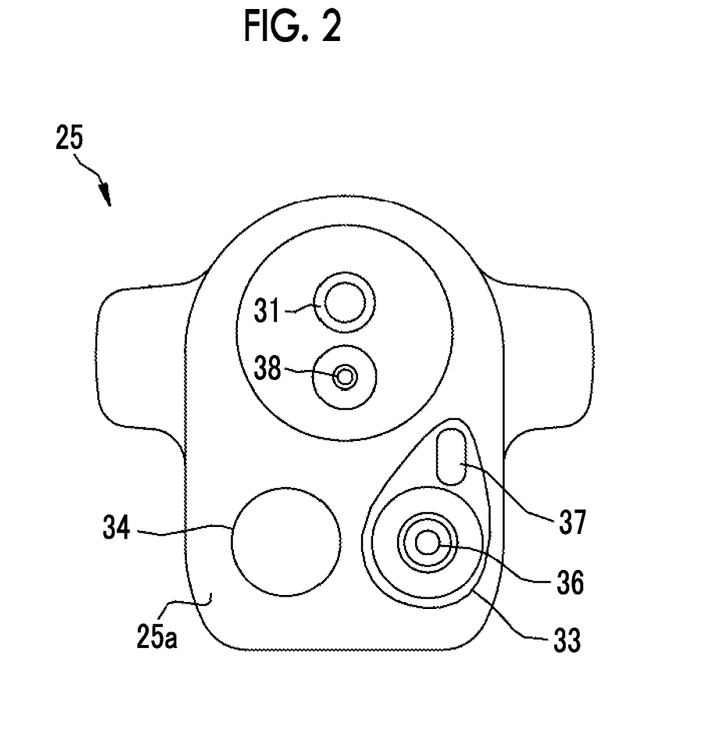
FIG. 2 is a plan view illustrating a connector-side connecting section.

As illustrated in FIG. 2, a connector-side connecting section 25a of the connector 25 comprises the light guide part 31 that guides the light from the light source device 14, a radio communication unit 33 that performs wireless communication with the light source device 14, and a power receiving unit 34 that wirelessly receives the supply of the electrical power from the light source device 14. The radio communication unit 33 has an image signal transmission unit 36 that wirelessly transmits digital image signals toward the light source device 14, and a control signal transmission/reception unit 37 that wirelessly transmit and receive the control signals to and from the light source device 14. The wireless communication performed by the image signal transmission unit 36 and the control signal transmission/reception unit 37 is optical communication, and is preferably near-infrared communication using, for example, near-infrared light (light having a wavelength of about 0.7 µm to 2.5 µm). Additionally, a pump connecting part 38 is provided below the light guide part 31 in the connector-side connecting section 25a.

The power receiving unit 34 is, for example, a coil (a so-called secondary coil), and receives the supply of the electrical power by a non-contact power transmission method, such as an electromagnetic induction method or a magnetic field resonance method, from a coil (a so-called primary coil) provided in the light source device 14. The power receiving unit 34 supplies the electrical power supplied from the light source device 14, to the respective units of the endoscope 12.

Figure 3:
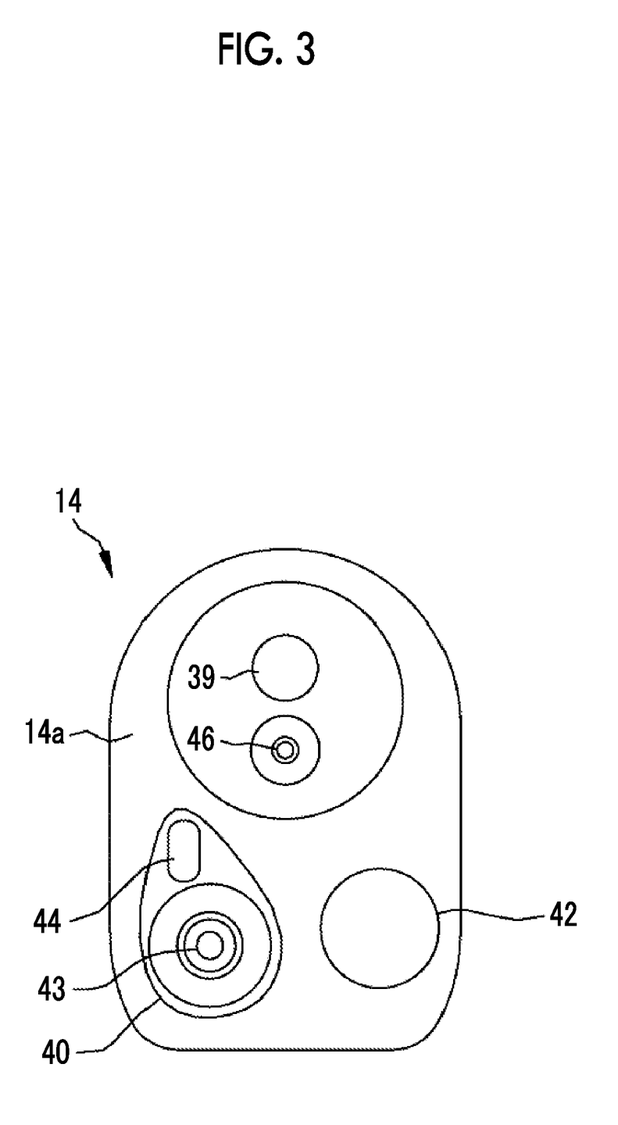
FIG. 3 is a plan view illustrating a light-source-device-side connecting section.

As illustrated in FIG. 3, the light source device 14 is provided with a light-source-device-side connecting section 14a that abuts against the connector-side connecting section 25a of the connector 25. The light-source-device-side connecting section 14a is provided with a light guide part insertion port 39 into which the light guide part 31 is inserted, a radio communication unit 40 that wirelessly communicates with the radio communication unit 33 of the connector 25, and a power feeding unit 42 that supplies the electrical power to the power receiving unit 34 of the connector 25. The radio communication unit 40 has an image signal reception unit 43 that wirelessly receives the digital image signals from the endoscope 12, and a control signal transmission/reception unit 44 that wirelessly transmits and receives the control signals to and from the endoscope 12. The power feeding unit 42 is, for example, a coil (so-called primary coil), and supplies the electrical power to the power receiving unit 34 by a non-contact power transmission method, such as an electromagnetic induction method or a magnetic field resonance method. Additionally, a pump connecting part insertion port 46 into which the pump connecting part 38 is inserted is provided below the light guide part insertion port 39 in the light-source-device-side connecting section 14a.

Figure 4:
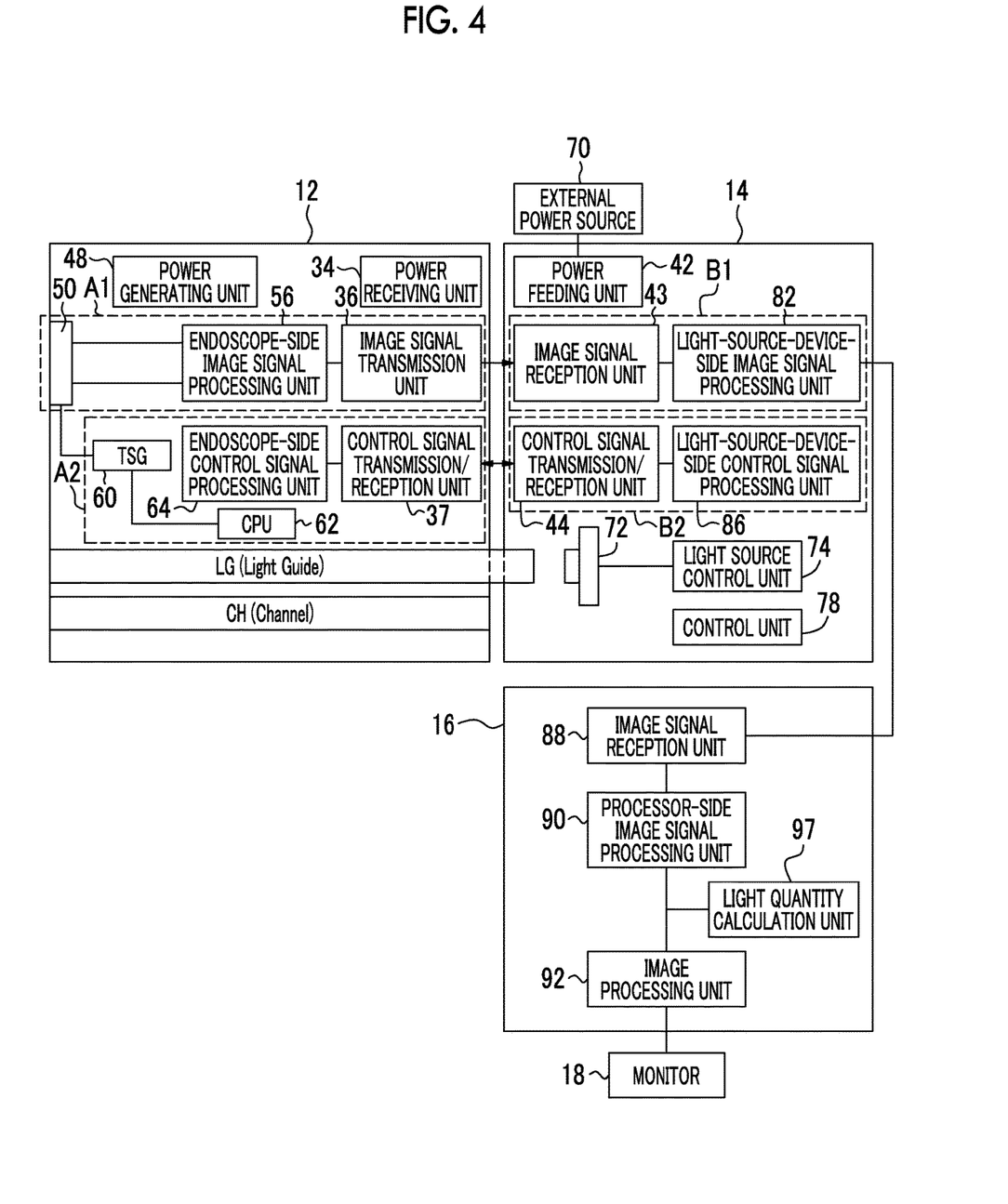
FIG. 4 is a block diagram illustrating functions of an endoscope, a light source device, and a processor device.

As illustrated in FIG. 4, the endoscope 12 is divided into an image signal area A1 for imaging the observation target to output the image signals and outputting the acquired image signals to the light source device 14, and a control signal area A2 for communicating the control signals with the light source device 14. Additionally, the endoscope 12 comprises a power generating unit 48 that generates various kinds of driving power required for respective parts, such as the image signal area A1 and the control signal area A2, and supplies the generated power. This power generating unit 48 receives the supply of the electrical power from the power receiving unit 34 that receives the electrical power from the light source device 14 in a contactless manner. In addition, the endoscope 12 comprises, in addition to the above, a light guide LG that guides the illumination light for illuminating the observation target, and a forceps channel CH (channel) for inserting various treatment tools, such as a high-frequency treatment tool.

In the image signal area A1, the endoscope 12 comprises an imaging unit 50 for imaging the observation target, an endoscope-side image signal processing unit 56 that performs various kinds of signal processing on the digital image signals, for the purpose of others, such as performing contactless optical transmission between the endoscope 12 and the light source device 14, and the image signal transmission unit 36 that converts the digital image signal into light signals and transmits the converted light signals toward the light source device 14.

In addition, the imaging unit 50 includes, for example, a solid-state imaging element such as a charge coupled device (CCD) image sensor or a complementary metal oxide semiconductor (CMOS) image sensor. In a case where the CCD is used as the imaging unit 50, an analog/digital (A/D) converter that converts analog image signals output from the imaging unit 50 into the digital image signals is provided in the endoscope 12. Additionally, the image signal transmission unit 36 is preferably a light emitting device capable of emitting light for optical communication, and includes, for example, light-emitting diodes or the like in addition to laser light emitting elements, such as a gas laser, a solid-state laser, and a semiconductor laser.

In the control signal area A2, the endoscope 12 includes a timing signal generator (TSG) 60 that generates signals for actuating the imaging unit 50, a central processing unit (CPU) 62 that controls driving of the TSG 60, an endoscope-side control signal processing unit 64 that performs various kinds of signal processing on the control signals used for the control or the like of the CPU 62 for other purposes, such as performing contactless optical transmission and reception between the endoscope 12 and the light source device 14, and the control signal transmission/reception unit 37 that transmits and receives the control signals between the endoscope 12 and the light source device 14. Here, the CPU 62 may control driving of various circuits provided in the endoscope 12 in addition to the TSG 60. In addition, the endoscope-side control signal processing unit 64 is constituted of, for example, a field programmable gate array (FPGA) and the like in addition to the central processing unit (CPU).

In addition, the control signal transmission/reception unit 37 comprises a light emitting device that optically transmits the control signals to the light source device 14 as the light signals, and a receiving device that receives the control signals from the light source device 14 as the light signals. Optical data communication of the optical contact by Infrared Data Association (IrDA) may be performed using, for example, an infrared light emitting element that optically transmits the control signals by infrared light and a light-receiving element (a photodiode, a phototransistor, or the like) that receives the optically signalized control signals, as the control signal transmission/reception unit 37.

The light source device 14 is divided into an image signal area B1 for receiving the digital image signals transmitted from the endoscope 12 and for sending the received digital image signals to the processor device 16, and a control signal area B2 for communicating various control signals with the endoscope 12. Additionally, an external power source 70 is connected to the light source device 14. The external power source 70 supplies electrical power to the respective units, such as the image signal area B1 and the control signal area B2, and also supplies the electrical power to the power feeding unit 42 that supplies the electrical power in a contactless manner to the endoscope 12.

In addition to the above, the light source device 14 comprises a light source 72 that emits the illumination light to be supplied to the light guide LG of the endoscope 12, and a light source control unit 74 that controls the light source 72. The light source 72 includes, for example, semiconductor devices, such as a laser diode and a light emitting diode, in addition to a xenon lamp. Additionally, the light source device 14 comprises a control unit 78 that controls the respective units, such as the image signal area and the control signal area, the respective units, such as the power feeding unit 42 and the light source control unit 74.

In the image signal area B1, the light source device 14 is provided with the image signal reception unit 43 that receives the light signals from the light source device 14 and converts the received light signals into the digital image signals, and a light-source-device-side image signal processing unit 82 that performs various kinds of signal processing on the digital image signals received by the image signal reception unit 43. The digital image signals subjected to the various kinds of signal processing by the light-source-device-side image signal processing unit 82 are transmitted to the processor device 16. In addition, the image signal reception unit 43 is constituted of receiving devices, such as a photodiode and a phototransistor.

In the control signal area B2, the light source device 14 is provided with the control signal transmission/reception unit 44 that transmits and receives the control signals between the endoscope 12 and the light source device 14, and a light-source-device-side control signal processing unit 86 that performs various kinds of signal processing on the control signals. Similarly to the control signal transmission/reception unit 37, the control signal transmission/reception unit 44 also comprises a light emitting device that optically transmits the control signals to the endoscope 12 as the light signals, and a receiving device that receives the control signals from the endoscope as the light signals. The specific examples of the light emitting device and the receiving device are the same as those of the control signal transmission/reception unit 37. In addition, it is preferable that the light-source-device-side control signal processing unit 86 is constituted of, for example, a field programmable gate array (FPGA) and the like in addition to the central processing unit (CPU).

The processor device 16 comprises an image signal reception unit 88 that receives the digital image signals from the light source device 14, a processor-device-side image signal processing unit 90 that performs various kinds of image processing on the digital image signals received by the image signal reception unit 88, and an image processing unit 92 that performs various kinds of signal processing on the digital image signals that have passed through the processor-device-side image signal processing unit 90, and generates display image data. The monitor 18 is connected to the processor device 16, and the monitor 18 displays an image of the observation target or the like on the basis of the display image data generated by the image processing unit 92. The processor device 16 is capable of communicating with the light source device 14. The various data obtained by the processor device 16 are sent to the light source device 14, and the various data are used for the control of the respective units within the light source device 14 in the control unit 78 within the light source device 14. In addition, it is preferable that the processor-device-side image signal processing unit 90 is constituted of, for example, a field programmable gate array (FPGA) and the like.

Figure 5:
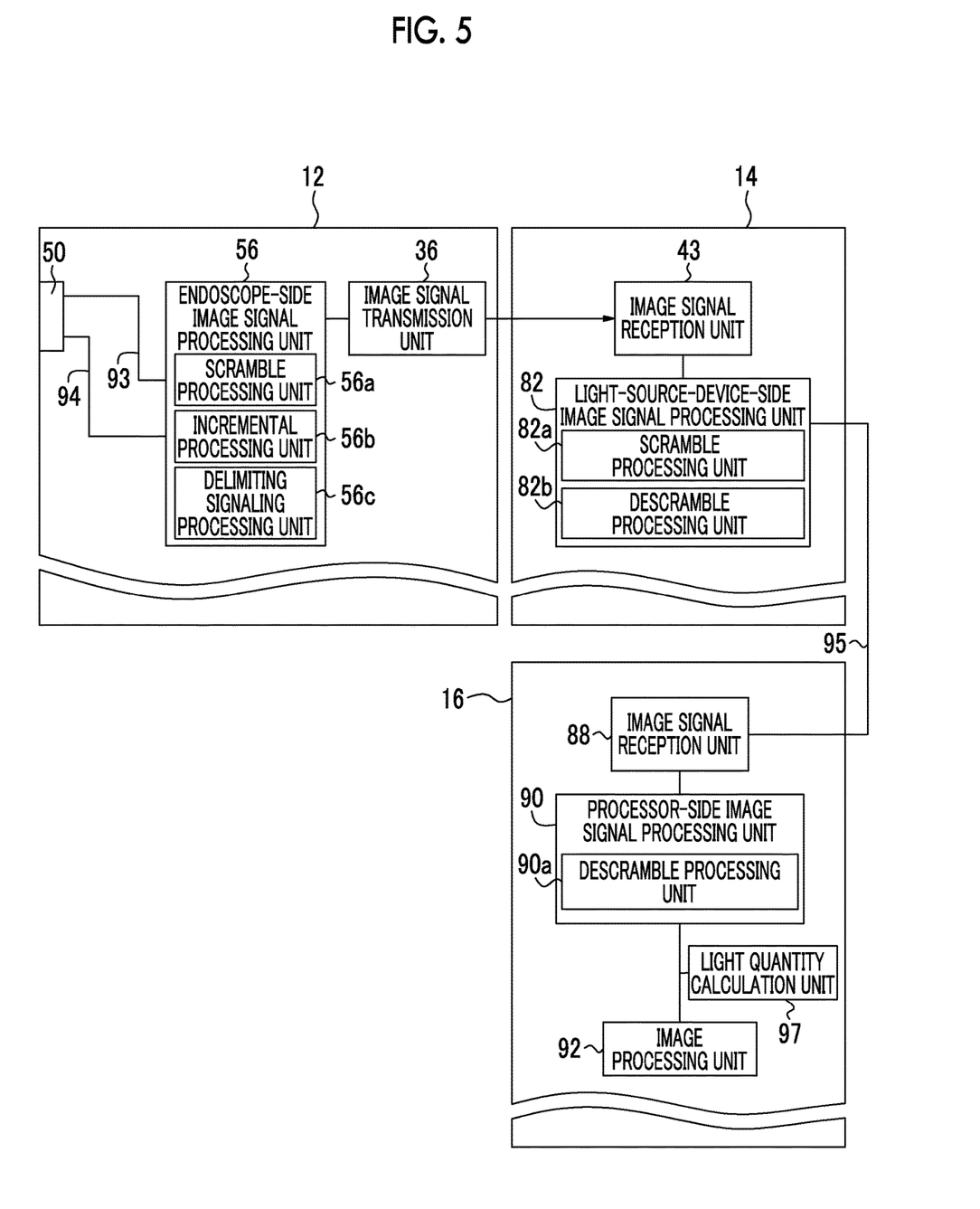
FIG. 5 is a block diagram illustrating functions of the endoscope comprising a scramble processing unit, the light source device, and the processor device comprising a descramble processing unit.

As illustrated in FIG. 5, the imaging unit 50 and the endoscope-side image signal processing unit 56 are connected to each other by two signal cables 93 and 94, and the digital image signals from the imaging unit 50 are transmitted to the endoscope-side image signal processing unit 56 through high-speed serial communication (for example, 528 MHz). In addition, the endoscope-side image signal processing unit 56 is constituted of, for example, a field programmable gate array (FPGA) and the like.

The endoscope-side image signal processing unit 56 comprises a scramble processing unit 56*a* that performs the scramble processing, and an incremental processing unit 56*b* that performs the incremental processing, as processing units that perform the processing of keeping the same data from being consecutive, on the received digital image signals in order to avoid electro-magnetic interference (EMI) generated as case where the same data is consecutive in the digital image signals. The details of the scramble processing and the incremental processing will be described below. The digital image signals subjected to the incremental processing or the scramble processing, which have passed through the endoscope-side image signal processing unit 56, are transmitted to the image signal transmission unit 36.

Additionally, the image signal transmission unit 36 and the image signal reception unit 43 are connected to each other in a contactless manner by one-channel optical communication, and the digital image signals subjected to the incremental processing or the scramble processing from the image signal transmission unit 36 are transmitted to the image signal reception unit 43 through high-speed serial communication. The digital image signals subjected to the incremental processing and the scramble processing, which have received by the image signal reception unit 43, are transmitted to the light-source-device-side image signal processing unit 82. The light-source-device-side image signal processing unit 82 comprises a scramble processing unit 82*a* that performs the scramble processing, and a descramble processing unit 82*b* that performs descramble processing on the received digital image signals.

In the present embodiment, the scramble processing and the descramble processing are not performed in the scramble processing unit 82*a* and the descramble processing unit 82*b*. However, in addition to or instead of the scramble processing unit 56*a* of the endoscope 12, the scramble processing may be performed by the scramble processing unit 82*a* within the light source device 14, and in addition to or instead of the descramble processing unit 90*a* of the processor device 16, the descramble processing may be performed by the descramble processing unit 82*b* within the light source device 14.

Additionally, the light-source-device-side image signal processing unit 82 and the processor-device-side image signal processing unit 90 are connected to each other by one or a plurality of signal cables 95, and the digital image signals from the light-source-device-side image signal processing unit 82 are transmitted to the processor-device-side image signal processing unit 90 through high-speed serial communication (for example, 2.112 GHz). In addition, it is preferable that the light-source-device-side image signal processing unit is constituted of, for example, a field programmable gate array (FPGA) and the like.

The processor-device-side image signal processing unit 90 comprises a descramble processing unit 90*a* that performs the descramble processing on the received scramble-processed digital image signals. The details of this descramble processing will be described below. The descramble-processed digital image signals are transmitted to the image processing unit 92, and various kinds of image processing are performed on the basis of the descramble-processed digital image signals in the image processing unit 92.

Figure 6:
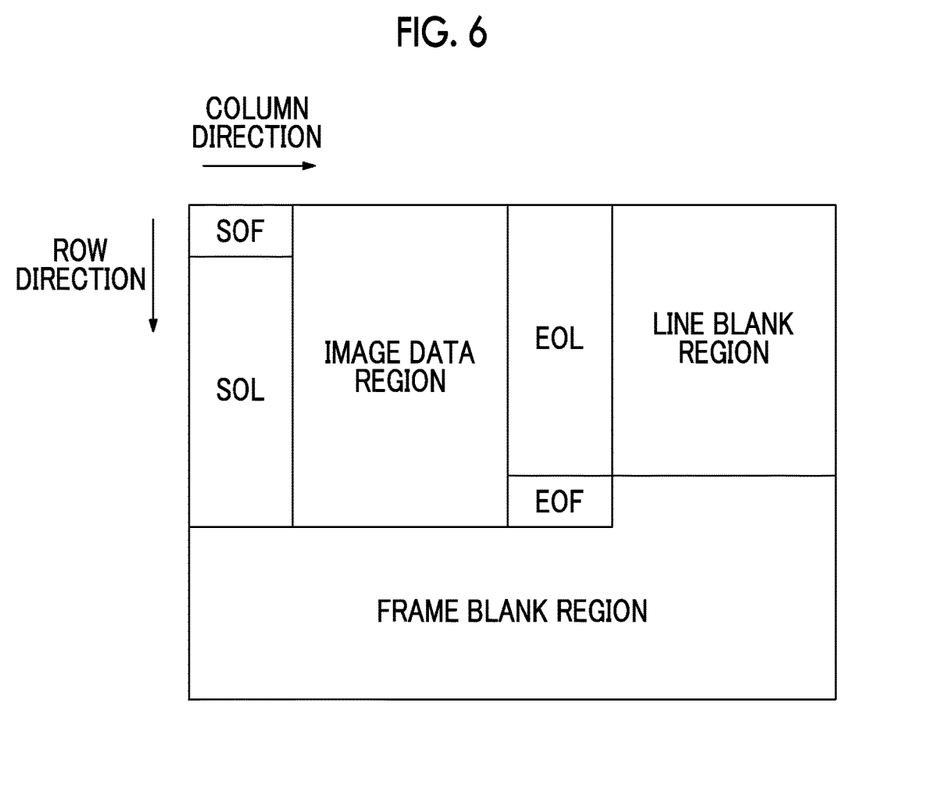
FIG. 6 is an explanatory view illustrating a digital image signal of a specific format.

The details of the scramble processing, incremental processing and the descramble processing will be described. In the present embodiment, a specific format illustrated in FIG.

6 is adopted for the digital image signals output from the imaging unit 50. In this specific format, in one frame of digital image signals, there are mainly three regions of an image data region, a line blank region, and a frame blank region.

The image data region has digital information on an image of an observation target by a specific number of pixels with respect to a row direction and a column direction. A start of the frame (SOF) indicating a start position of the image data region, an end of a line (EOL) indicating an end position of an n-th row (n is a natural number equal to or greater than and 1 and equal to or smaller than M) of the image data region, a start of the line (SOL) indicating a start position of an (n+1)th row, and an end of the frame (EOF) indicating an end position of an M-th row that is the last row of the image data region are provided before and after this image data region.

The line blank region is a region for outputting any values having no digital information on the image of the observation target between the EOL in the n-th row and the SOL in the next (n+1)th row. A frame blank region is a region for outputting any values having no the digital information on the image of an observation target between EOF and the N-th row that is the last row of the one frame of digital image signals.

Hence, the one frame of digital image signals is output from the imaging unit 50 as follows. First, the SOF is output, and thereafter, data in the first row of the image data region is output. In a case where an EOF in the first row is output, data in the line blank region is output until an SOL in the second row is output. After the SOL in the second row is output, data in the second row of the image data region is output. Thereafter, data in the image data region and the line blank region are output similarly up to the M-th row. After the EOF is output, the data of the frame blank region is output up to the N-th row that is the last row.

In addition, in the specific format, the number of pixels equivalent to one frame is determined to be constant irrespective of the size of the number of pixels of the image data region. For that reason, the larger the number of pixels of the image data region, the smaller the number of pixels of the line blank region or the frame blank region. On the contrary, the smaller the number of pixels of the image data region, the larger the number of pixels of the line blank region or the frame blank region. That is, the line blank region or the frame blank region is a region for adjusting the number of pixels equivalent on one frame depending on the number of pixels of the image data region.

Since the line blank region or the frame blank region is a region having no digital information on the image of the observation target, this region is usually a region where the same data (for example, "0"s) are consecutive. As the same bits are consecutive in this way, the electro-magnetic interference (EMI) is likely to occur. Then, the same bits are kept from being consecutive by performing the incremental processing on the line blank region or the frame blank region.

Figure 7:
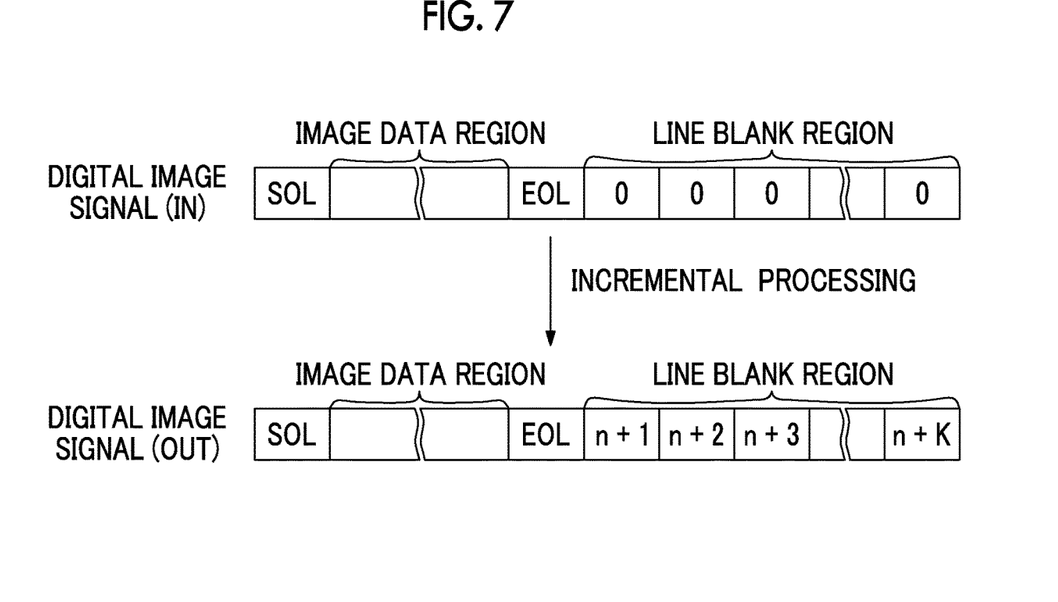
FIG. 7 is an explanatory view illustrating incremental processing.

For example, as illustrated in FIG. 7, in a case where digital image signals (IN) in which "0"s are consecutive in the line blank region are input to the incremental processing unit 56b, digital image signals (OUT) are output by performing the incremental processing on the line blank region. For example, in a case where of different kinds of the incremental processing are performed for every row (every line), a line blank region in the n-th row of the digital image signals (OUT) becomes a region where the same bits are not consecutive, like "n+1" and "n+2", . . . and "n+K (three or more natural numbers)". Accordingly, since this can prevent concentration of serial communication clocks to multiplied frequencies can be prevented, occurrence of the electro-magnetic interference (EMI) can be avoided.

In addition, although the different kinds of incremental processing are performed for every row (every line) in the above incremental processing, the same incremental processing may be performed for all the rows. Here, in a case where the different kinds of incremental processing are performed for every row (every line), it is preferable to provide a line number region having information on line numbers.

Since the image data region is a region having the digital information on the image of the observation target unlike the line blank region or the frame blank region, the same data is not consecutive unless halation or the like occurs. However, in a case where the halation or the like occurs and a pixel is saturated, the same data (data Mx representing the highest pixel value) is consecutive for a portion having the saturated pixel. In this way, in a case where the same data Mx is consecutive, the electro-magnetic interference (EMI) is likely to occur. Thus, in order to avoid the electro-magnetic interference, the scramble processing unit 56a performs the scramble processing on the image data region. Then, in the descramble processing unit 90a, the image of the observation target is restored by performing the descramble processing on the image scramble-processed image data region.

Figure 8:
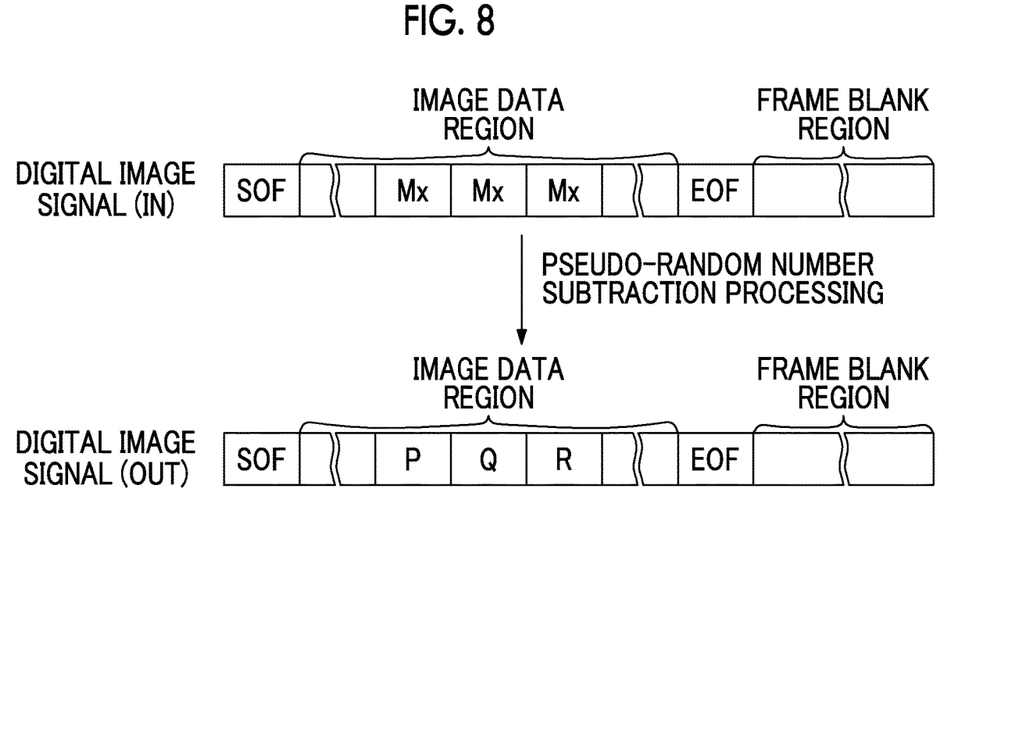
FIG. 8 is an explanatory view illustrating pseudo-random number subtraction processing.

In the present embodiment, pseudo-random number subtraction processing in which a pseudo-random number is subtracted from the image data region is performed as the scramble processing for the image data region. As illustrated in FIG. 8, in a case where the digital image signals (IN) having a pixel region where the same data Mx is consecutive in the image data region are input to the scramble processing unit 56a, the digital image signals (OUT) subjected to the pseudo-random number subtraction processing are output by performing the pseudo-random number subtraction processing. In the digital image signals (OUT) subjected to the pseudo-random number subtraction processing, a region where the same data Mx is consecutive in the digital image signals (IN) becomes a region where the same data is no longer consecutive like "P", "Q", and "R". Accordingly, occurrence of the electro-magnetic interference (EMI) can be avoided.

Figure 9:
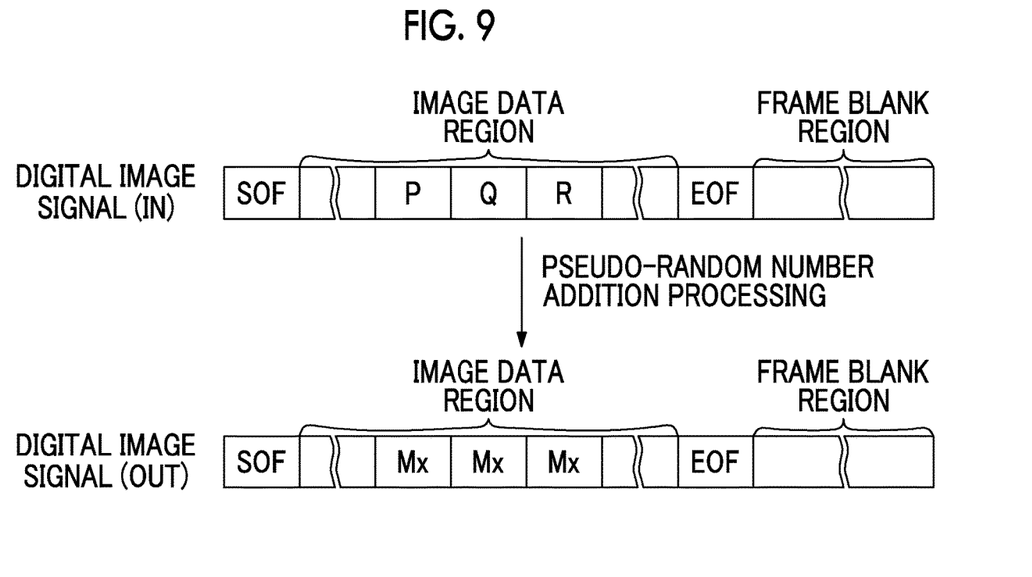
FIG. 9 is an explanatory view illustrating pseudo-random number addition processing.

Then, in a case where the pseudo-random number subtraction processing is performed as the scramble processing, pseudo-random number addition processing in which a pseudo-random number is added to the image data region is performed as the descramble processing. As illustrated in FIG. 9, in a case where the digital image signals (IN) that become the region where the same data is not consecutive are input to the descramble processing unit 90a like "P", "Q", and "R" by the pseudo-random number subtraction processing, the digital image signals (OUT) subjected to the pseudo-random number addition are output by performing the pseudo-random number addition processing. In the digital image signals subjected to the pseudo-random number addition, the region where the same data is not consecutive in the digital image signals (IN) is restored to a region where the same data is consecutive as "Mx", "Mx", and "Mx". Accordingly, the image of the observation target is restored.

In addition, in the pseudo-random number subtraction processing or the pseudo-random number addition processing, first, an M-series random number is generated in a case where SOL is detected. Then, it is preferable to allocate lower 8 bits of the generated 16-bit random numbers to the image data region of the digital image signals transmitted by the signal cable 93 (refer to FIG. 5), and to allocate upper 8 bits to the image data region of the digital image signals transmitted by the signal cable 94 (refer to FIG. 5), to perform the pseudo-random number subtraction processing or the pseudo-random number addition processing.

Figure 10:
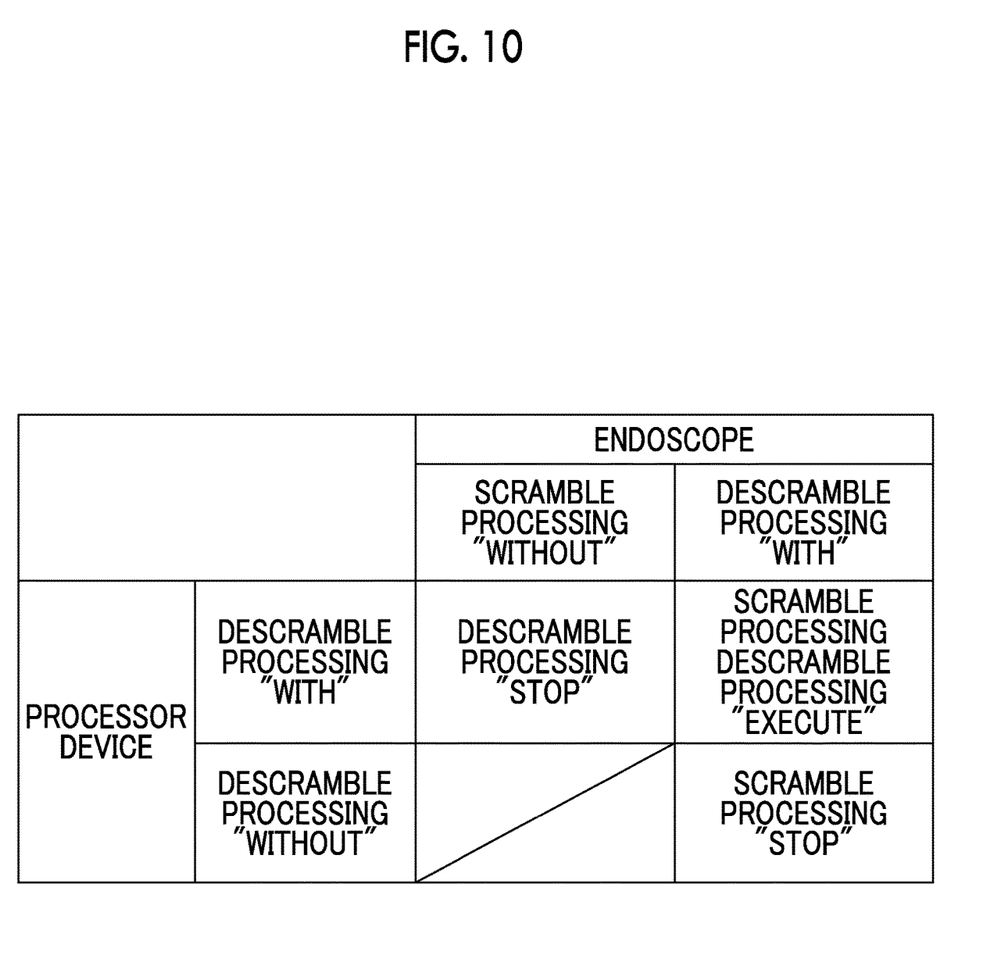
FIG. 10 is a table illustrating that scramble processing or descramble processing is executed or stopped by combinations of the endoscope and the processor device.

Next, in a case where the endoscope 12 is mounted on the light source device 14 and is brought into a state where the endoscope 12 is communicable with the processor device 16, as illustrated in FIG. 10, the scramble processing and the descramble processing are executed only in a case where a scramble processing function is present on the endoscope 12 side and a descramble function is present on the processor device 16 side. In contrast, even in a case where the scramble processing function is present on the endoscope 12 side, the scramble processing function of the endoscope 12 is stopped in a case where there is no descramble processing function on the processor device 16 side. In such a case, this is because the image of the observation target is affected in a case where the scramble processing is performed on the endoscope 12 side. Additionally, in a case where the descramble function is present on the processor device 16 side but there is no scramble function on the endoscope 12 side, the descramble processing is not executed. Even in this case, this is because the image of the observation target is affected in a case where the descramble processing is performed on the processor device 16 side.

As described above, only in a case where the endoscope 12 has the scramble processing function and the processor device 16 has the descramble processing function, the scramble processing and the descramble processing are executed. Therefore, the following processing is performed in a case where the endoscope 12 is mounted on the light source device 14.

First, the descramble processing unit 90*a* is brought into a state where the descramble processing is stopped in a state where the endoscope 12 is detached from the light source device 14. Then, in a case where the endoscope 12 is mounted on the light source device 14, the communication between the scramble processing unit 56*a* of the endoscope 12 and the descramble processing unit 90*a* of the processor device 16 becomes possible, the processor device 16 performs a request sequence in which a request signal for requesting the start of execution of the scramble processing is transmitted to the endoscope 12.

Figure 11:
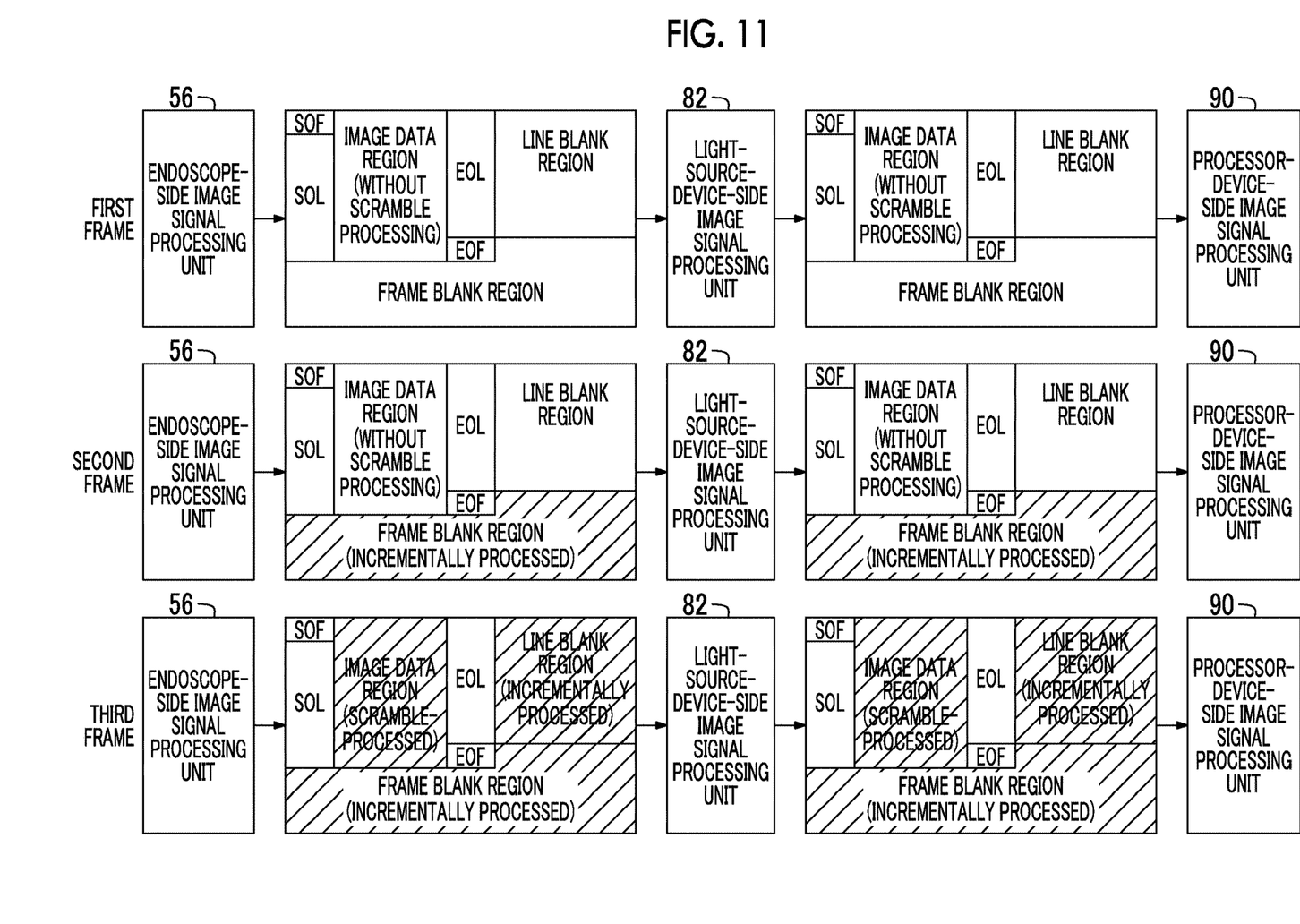
FIG. 11 is an explanatory view illustrating an initial transmission sequence.

Next, in the endoscope 12 that has received the request signal, an initial transmission sequence in which the digital image signals obtained by imaging the observation target are transmitted to the processor device 16 is performed. In this initial transmission sequence, as illustrated in FIG. 11, digital image signals of a first frame obtained after the mounting of the endoscope 12 are transmitted to the light-source-device-side image signal processing unit 82 without being scramble-processed and incrementally processed by the endoscope-side image signal processing unit 56. The digital image signals received by the light-source-device-side image signal processing unit 82 are transmitted to the processor-device-side image signal processing unit 90 as they are.

Regarding digital image signals of the next second frame, the endoscope-side image signal processing unit 56 performs the incremental processing only in the frame blank region, and the digital image signals incrementally processed only in this frame blank region are transmitted to the light-source-device-side image signal processing unit 82 (a first transmission sequence). In the light-source-device-side image signal processing unit 82, in a case where the digital image signals incrementally processed only in the frame blank region are received, it is recognized that the mounted endoscope 12 has the scramble processing function of avoiding the electro-magnetic interference. The digital image signals received by the light-source-device-side image signal processing unit 82 are transmitted to the processor-device-side image signal processing unit 90 as they are.

Then, in the processor-device-side image signal processing unit 90, by receiving the digital image signals of the second frame incrementally processed in the frame blank region, it is recognized that the mounted endoscope 12 has the scramble processing function of avoiding the electro-magnetic interference. Accordingly, the execution of the descramble processing is started.

Regarding digital image signals of the next third frame, not only the incremental processing is performed on the frame blank region, but also the scramble processing is performed on the image data region and the line blank region, and the scramble-processed and incrementally-processed digital image signals are transmitted to the light-source-device-side image signal processing unit 82 (a second transmission sequence). The digital image signals received by the light-source-device-side image signal processing unit 82 are transmitted to the processor-device-side image signal processing unit 90 as they are. Then, the processor-device-side image signal processing unit 90 performs the descramble processing on the received digital image signals.

As described above, switching to a countermeasure mode for avoiding the electro-magnetic interference can be reliably made by performing the recognition that the endoscope 12 comprises the scramble processing function of avoiding the electro-magnetic interference in order of the endoscope-side image signal processing unit 56 the light-source-device-side image signal processing unit 82→the processor-device-side image signal processing unit 90 over the two frames.

In addition, in the above embodiment, the pseudo-random number subtraction processing and the pseudo-random number addition processing are always performed on the image data region of the digital image signals. However, the pseudo-random number subtraction processing and the pseudo-random number addition processing may be performed only in a case where high-luminance states, such as halation, have occurred. In this case, a light quantity calculation unit 97 (refer to FIG. 4) provided in the processor device 16 calculates the quantity of light on the basis of the digital image signals. Then, in a case where the quantity of light is less than a fixed value, the scramble processing unit 56*a* stops the pseudo-random number subtraction processing, and the descramble processing unit 90*a* stops the pseudo-random number addition processing. On the other hand, in a case where the quantity of light reaches a fixed value or more, the scramble processing unit 56*a* executes the pseudo-random number subtraction processing, and the descramble processing unit 90*a* executes the pseudo-random number addition processing.

Figure 12:
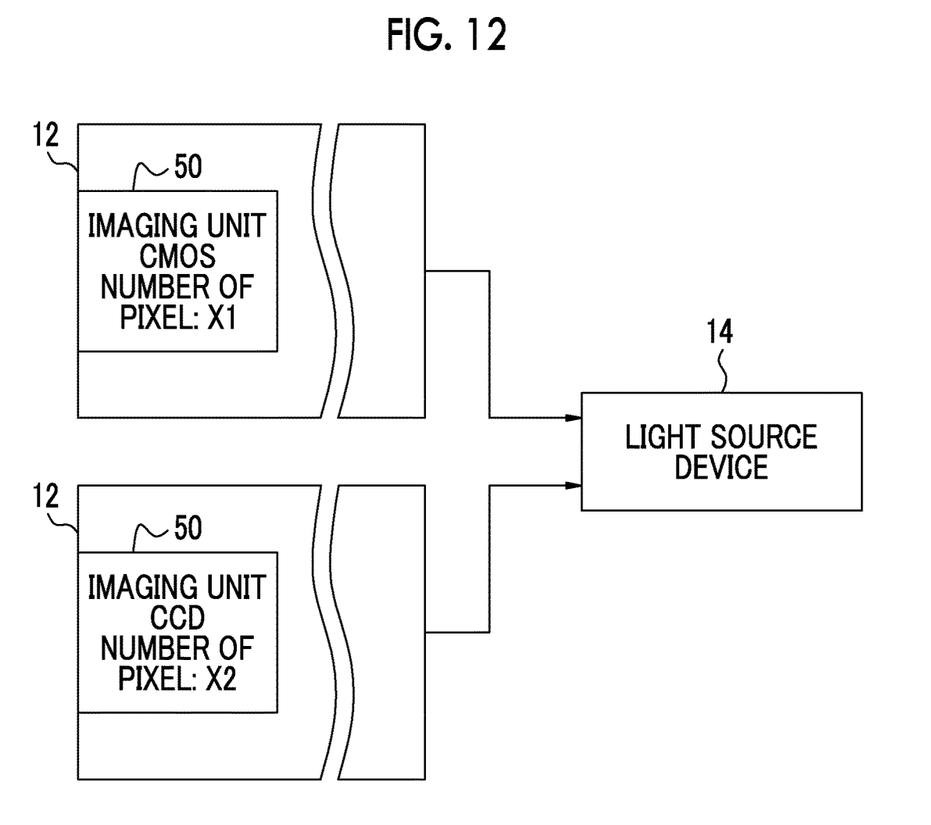
FIG. 12 is an explanatory view illustrating the scramble processing and the descramble processing in a case where endoscopes having different types of imaging units or different numbers of pixels are used.

In addition, in the above embodiment, a plurality of endoscopes 12 having different types of the imaging units 50 and different numbers of pixels may be mounted on the light source device 14. In this case, it is preferable that, even in a case where any endoscope 12 is mounted, the scramble processing and the descramble processing can be reliably performed, and in any endoscope 12, the digital image signals are output in a specific format from the imaging unit 50.

For example, as illustrated in FIG. 12, in a case where both the endoscope 12 in which the imaging unit 50 has a X1 pixel number in the CMOS, and the endoscope 12 in which the imaging unit 50 has a X2 pixel number (different from X1) in the CCD are mountable on the light source device 14, the numbers of pixels are different from each other as X1 and X2, but the image data region is specified by the SOF and the EOF by adopting the specific format. Therefore, the scramble processing and the descramble processing can be reliably performed on the image data region.

In addition, in the above embodiment, a case where electric noise is mixed into the signal cables 93 and 94 that transmit the digital image signals, and the digital image signals are broken is assumed. In the present embodiment, the scramble processing is performed on the digital image signals. Therefore, in a case where such scramble-processed digital image signals are broken due to electric noise or the like, the endoscope 12 or processor device 16 cannot know that data at any point among the digital image signals has been transmitted or received. Hence, it is preferable to add a marker to the digital image signals so that it is possible to know that the endoscope 12 or the processor device 16 has transmitted or received data up to any point. In addition, as a situation in which electric noise is mixed, in a case where a high-frequency treatment tool is inserted through the forceps channel CH that is juxtaposed with the signal cables 93 and 94 in the endoscope 12, a situation in which the electric noise emitted from the high-frequency treatment tool is mixed into the signal cables 93 and 94 is considered.

Figure 13:
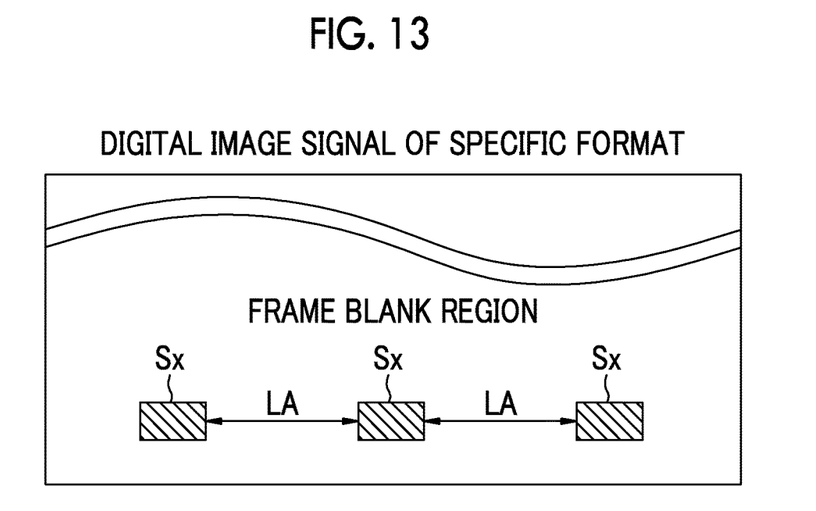
FIG. 13 is an explanatory view illustrating delimiting signaling processing.

For example, as illustrated in FIG. 13, delimiting signaling processing in which delimiter signals Sx are applied at regular intervals LA is performed on the digital image signals subjected to the incremental processing and scramble processing (in FIG. 13, only some of the delimiter signals Sx are illustrated in order to avoid that the drawing becomes complicated). Then, in the digital image signals to which the delimiter signals Sx are applied, the delimiter signals are read in the descramble processing unit 90a. Accordingly, it is possible to know that data up to any point among the digital image signals has been received. In addition, it is preferable that the delimiter signals Sx are fixed values. Additionally, it is preferable to apply the delimiter signals Sx for one pixel. Additionally, it is preferable that the intervals LA at which the delimiter signals Sx are applied are a cycle of the incremental processing to be performed on the line blank region or the frame blank region. In addition, it is preferable that a delimiting signaling processing unit 56c (refer to FIG. 5) that performs the delimiting signaling processing is provided in the endoscope-side image signal processing unit 56 of the endoscope 12.

In addition, in the above embodiment, the pseudo-random number subtraction processing or the pseudo-random number addition processing is performed on the image data region, and the incremental processing is performed on the line blank region and the frame blank region. However, the scramble processing and the descramble processing may be performed by the other methods. For example, instead of the incremental processing, the pseudo-random number subtraction processing or the pseudo-random number addition processing may be performed on the line blank region and the frame blank region. Additionally, although the scramble processing and the descramble processing are performed on the digital image signals, the scramble processing and the descramble processing may be applied on the control signals in addition to these.

In addition, in the above embodiment, the scramble processing unit 56a and the descramble processing unit 90a are brought into a communicable state by mounting the endoscope 12 on the light source device 14 connected to the processor device 16. However, the scramble processing unit 56a and the descramble processing unit 90a may be brought into the communicable state by directly mounting the endoscope 12 on the processor device 16.

In addition, in the above embodiment, it is preferable to perform, for example, 8-bit/10-bit conversion on data corresponding to respective pixels of the image signals, as bit conversion for the image signals.

In addition, in the above embodiment, the scramble processing is performed on the digital image signals obtained by the endoscope 12. However, not only the scramble processing but also encoding processing, such as signal processing to be restored later may be performed. In this case, instead of the scramble processing unit 56a, an encoding processing unit (not illustrated) performs the encoding processing. Additionally, in the above embodiment, the descramble processing is performed on the scramble-processed digital image signals from the endoscope 12. However, not only the descramble processing but also decoding processing, such as signal processing in which the encoding-processed signals are restored may be performed. In this case, instead of the descramble processing unit 90a and the like, a decoding processing unit (not illustrated) performs the decoding processing.

EXPLANATION OF REFERENCES

10: endoscope system
12: endoscope
14: light source device
14a: light-source-device-side connecting section
16: processor device
18: monitor
20: console
21: insertion part
22: operating part
23: universal cable
25: connector
25a: connector-side connecting section
31: light guide part
33: radio communication unit
34: power receiving unit
36: image signal transmission unit
37: control signal transmission/reception unit
38: pump connecting part
39: light guide part insertion port
40: radio communication unit
42: power feeding unit
43: image signal reception unit
44: control signal transmission/reception unit
46: pump connecting part insertion port
48: power generating unit
50: imaging unit
56: endoscope-side image signal processing unit
56a: scramble processing unit (equivalent to "encoding processing unit" of the invention)
56b: incremental processing unit
56c: delimiting signaling processing unit
60: TSG
62: CPU
64: endoscope-side control signal processing unit
70: external power source
72: light source
74: light source control unit
78: control unit
82: light-source-device-side image signal processing unit
82a: scramble processing unit (equivalent to "encoding processing unit" of the invention)

82*b*: descramble processing unit (equivalent to "decoding processing unit" of the invention)
86: light-source-device-side control signal processing unit
90: processor-device-side image signal processing unit
90*a*: descramble processing unit (equivalent to "decoding processing unit" of the invention)
92: image processing unit
93: signal cable
94: signal cable
95: signal cable
97: light quantity calculation unit

What is claimed is:

1. An endoscope system comprising at least any one of a processor device that is attachable to and detachable from an endoscope or a light source device that is attachable to and detachable from the endoscope,
wherein in a case where the endoscope is mounted on the processor device or the light source device, a request sequence is performed in which a request signal, for requesting a start of execution of encoding processing with respect to digital image signals, is transmitted from the processor device or the light source device to the endoscope,
wherein in a case where the endoscope comprises an encoding processing unit configured to execute the encoding processing, the encoding processing unit starts execution of the encoding processing with reception of the request signal as a trigger, and performs an initial transmission sequence in which digital image signals are transmitted to the processor device or the light source device,
wherein in a case where the endoscope has a scramble processing function and the processor device has a descramble processing function and the endoscope is mounted on the light source device, the request sequence is performed in which the request signal, for requesting a start of execution of scramble processing, is transmitted from the processor device or the light source device to the endoscope, wherein the scramble process scrambles consecutive bits of the digital image signals having the same value to avoid electro-magnetic interferences caused by the consecutive bits having the same value.

2. The endoscope system according to claim 1,
wherein the initial transmission sequence comprises:
a first transmission sequence in which signal processing is performed on a specific region other than an image data region having image information on an observation target in the digital image signals, and the digital image signals subjected to the signal processing are transmitted to the processor device or the light source device, and
a second transmission sequence in which the encoding processing is performed on the digital image signals after the first transmission sequence, and the digital image signals subjected to the encoding processing are transmitted to the processor device or the light source device.

3. The endoscope system according to claim 2,
wherein the signal processing is incremental processing.

4. The endoscope system according to claim 2,
wherein the specific region is a line blank region or a frame blank region.

5. The endoscope system according to claim 1, further comprising:
a light quantity calculation unit is configured to calculate the quantity of light in an observation target on the basis of the digital image signals,
wherein the encoding processing unit is configured to switch between execution and stop of the encoding processing depending on the quantity of light.

6. The endoscope system according to claim 5,
wherein the encoding processing unit is configured to stop the encoding processing in a case where the quantity of light is less than a fixed value, and is configured to execute the encoding processing in a case where the quantity of light is equal to or more than the fixed value.

7. The endoscope system according to claim 1, further comprising:
a delimiting signaling processing unit is configured to execute delimiting signaling processing in which delimiter signals are applied to the digital image signals subjected to the encoding processing at regular intervals.

8. The endoscope system according to claim 1,
wherein in a case where the processor device or the light source device comprises a decoding processing unit is configured to execute decoding processing on the digital image signals subjected to the encoding processing, the decoding processing unit starts execution of the decoding processing with reception of the digital image signals subjected to the encoding processing as a trigger.

9. The endoscope system according to claim 1,
wherein in a case where the processor device or the light source device comprises a decoding processing unit configured to execute decoding processing on the digital image signals subjected to the encoding processing, the decoding processing unit stops execution of the decoding processing with reception of the digital image signals as a trigger.

10. The endoscope system according to claim 1,
wherein the encoding processing is scramble processing including pseudo-random number subtraction processing in which a pseudo-random number is subtracted from the digital image signals.

11. A method of operating an endoscope system including at least any one of a processor device that is attachable to and detachable from an endoscope or a light source device that is attachable to and detachable from the endoscope, the method comprising:
a step of performing, by the processor device or the light source device, a request sequence in which a request signal for requesting a start of execution of encoding processing with respect to digital image signals is transmitted to the endoscope in a case where the endoscope is mounted on the processor device or the light source device,
wherein in a case where the endoscope comprises an encoding processing unit configured to execute the encoding processing, and the method further comprises: starting, by the encoding processing unit, execution of the encoding processing with reception of the request signal as a trigger, and performing an initial transmission sequence in which digital image signals are transmitted to the processor device or the light source device,
wherein in a case where the endoscope has a scramble processing function and the processor device has a descramble processing function and the endoscope is mounted on the light source device, the request sequence is performed in which the request signal, for requesting a start of execution of scramble processing, is transmitted from the processor device or the light source device to the endoscope, wherein the scramble process scrambles consecutive bits of the digital image signals having the same value to avoid electro-magnetic interferences caused by the consecutive bits having the same value.

* * * * *